(12) United States Patent
Chen et al.

(10) Patent No.: US 8,521,304 B2
(45) Date of Patent: Aug. 27, 2013

(54) MRI COMPATIBLE IMPLANTABLE LEAD WITH A DISTRIBUTED BAND STOP FILTER

(75) Inventors: Xiangqun Chen, Valencia, CA (US); Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 501 days.

(21) Appl. No.: 12/774,615

(22) Filed: May 5, 2010

(65) Prior Publication Data

US 2010/0318164 A1 Dec. 16, 2010

Related U.S. Application Data

(60) Provisional application No. 61/187,154, filed on Jun. 15, 2009.

(51) Int. Cl.
*A61N 1/00* (2006.01)
*A61M 25/00* (2006.01)

(52) U.S. Cl.
USPC ............... 607/116; 607/36; 607/37; 600/435

(58) Field of Classification Search
USPC ............... 607/36–37, 116; 600/435
See application file for complete search history.

(56) References Cited

U.S. PATENT DOCUMENTS

| | | | |
|---|---|---|---|
| 7,123,013 B2 | 10/2006 | Gray | |
| 7,174,219 B2 | 2/2007 | Wahlstrand et al. | |
| 2005/0070972 A1 | 3/2005 | Wahlstrand et al. | |
| 2005/0222647 A1 | 10/2005 | Wahlstrand et al. | |
| 2005/0222658 A1 | 10/2005 | Hoegh et al. | |
| 2006/0247747 A1 | 11/2006 | Olsen et al. | |
| 2006/0247748 A1 | 11/2006 | Wahlstrand et al. | |
| 2007/0112398 A1 | 5/2007 | Stevenson et al. | |
| 2007/0168006 A1 | 7/2007 | Gray | |
| 2008/0033497 A1 | 2/2008 | Bulkes et al. | |
| 2008/0049376 A1 | 2/2008 | Stevenson et al. | |
| 2008/0132986 A1 | 6/2008 | Gray et al. | |
| 2008/0161886 A1 | 7/2008 | Stevenson et al. | |
| 2008/0262584 A1* | 10/2008 | Bottomley et al. | 607/119 |
| 2009/0099440 A1 | 4/2009 | Viohl | |
| 2009/0099555 A1 | 4/2009 | Viohl et al. | |

FOREIGN PATENT DOCUMENTS

| | | |
|---|---|---|
| EP | 1883449 B1 | 1/2009 |
| EP | 2025361 A1 | 2/2009 |
| WO | 2005102445 A1 | 11/2005 |
| WO | 2005102446 A1 | 11/2005 |

* cited by examiner

*Primary Examiner* — Nicole F Lavert

(57) ABSTRACT

An implantable lead includes a lead body having a proximal end portion and a distal end portion with a connector located at the proximal end and an electrode located at the distal end. The implantable lead further includes a coil conductor that has spiral sections wound within a lumen of the lead body and couples the lead connector to the electrode. The coil conductor has an insulation material provided on at least a segment of the coil conductor. The insulation material has a dielectric constant set such that the coil conductor forms a distributed band stop filter when exposed to a known RF magnetic field. The coil conductor comprises a filar wound into the spiral sections. The filar of the coil conductor has an insulation coating provided thereon with the insulation coating forming a dielectric layer between adjacent spiral sections of the filar.

10 Claims, 9 Drawing Sheets

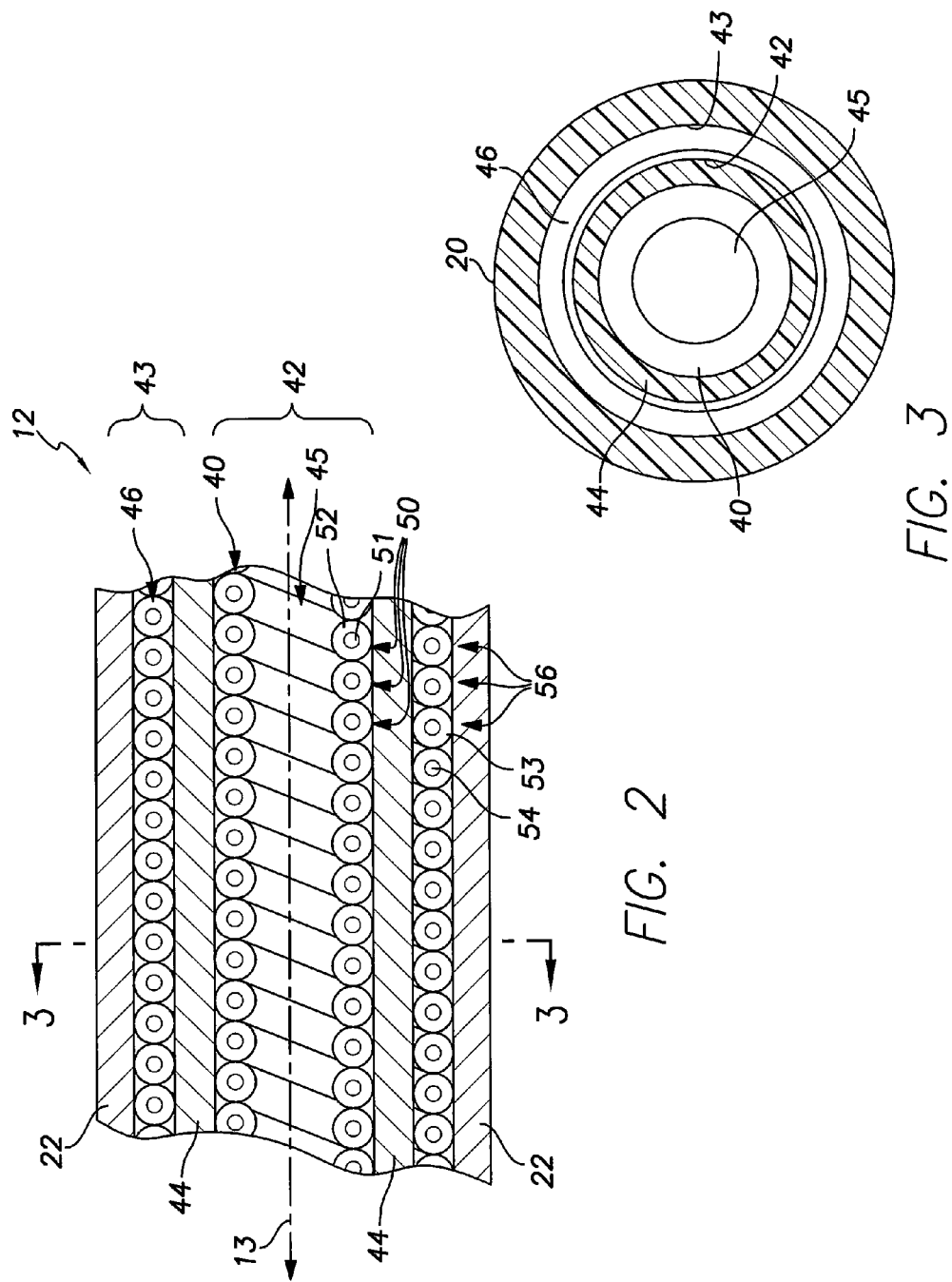

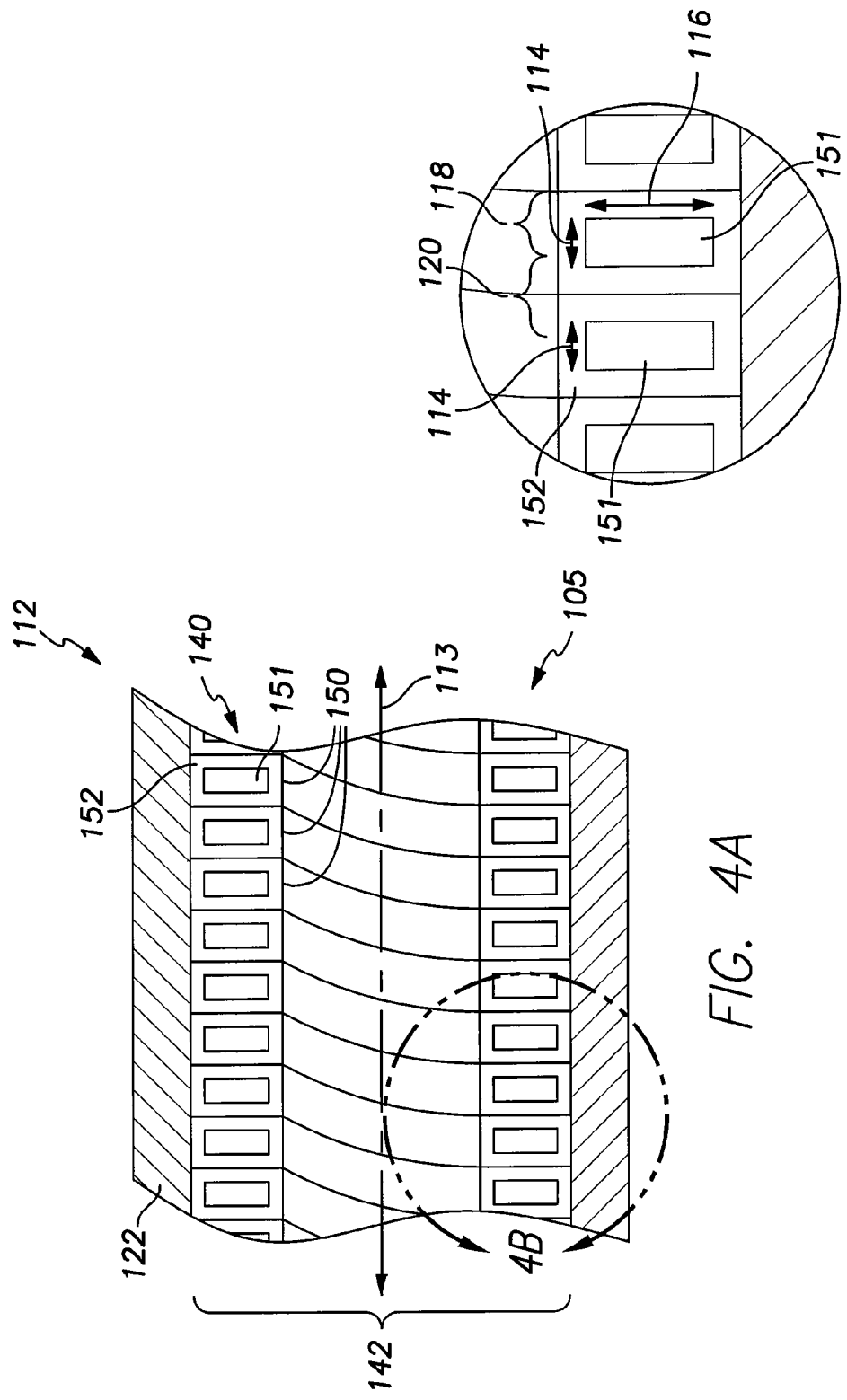

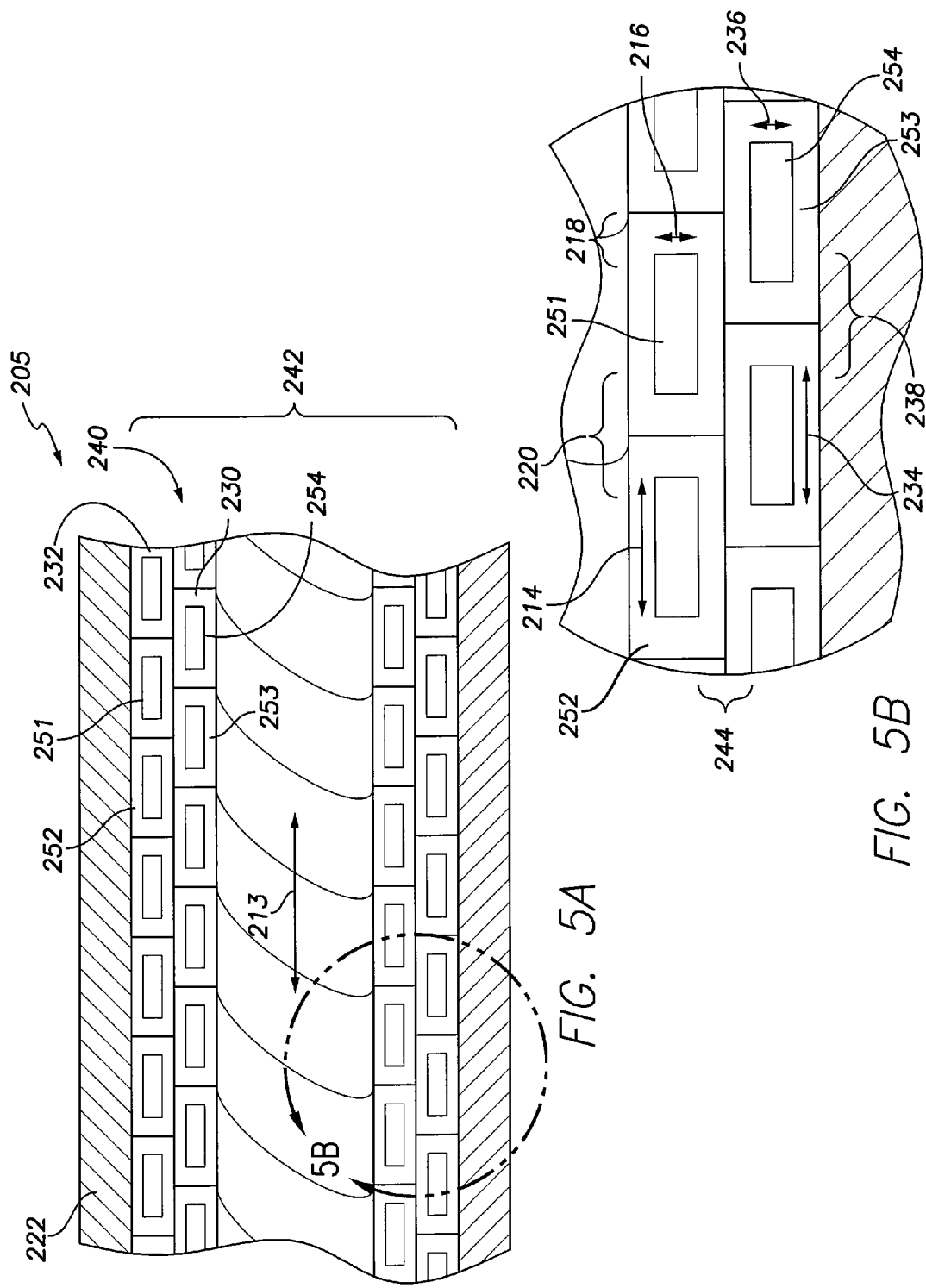

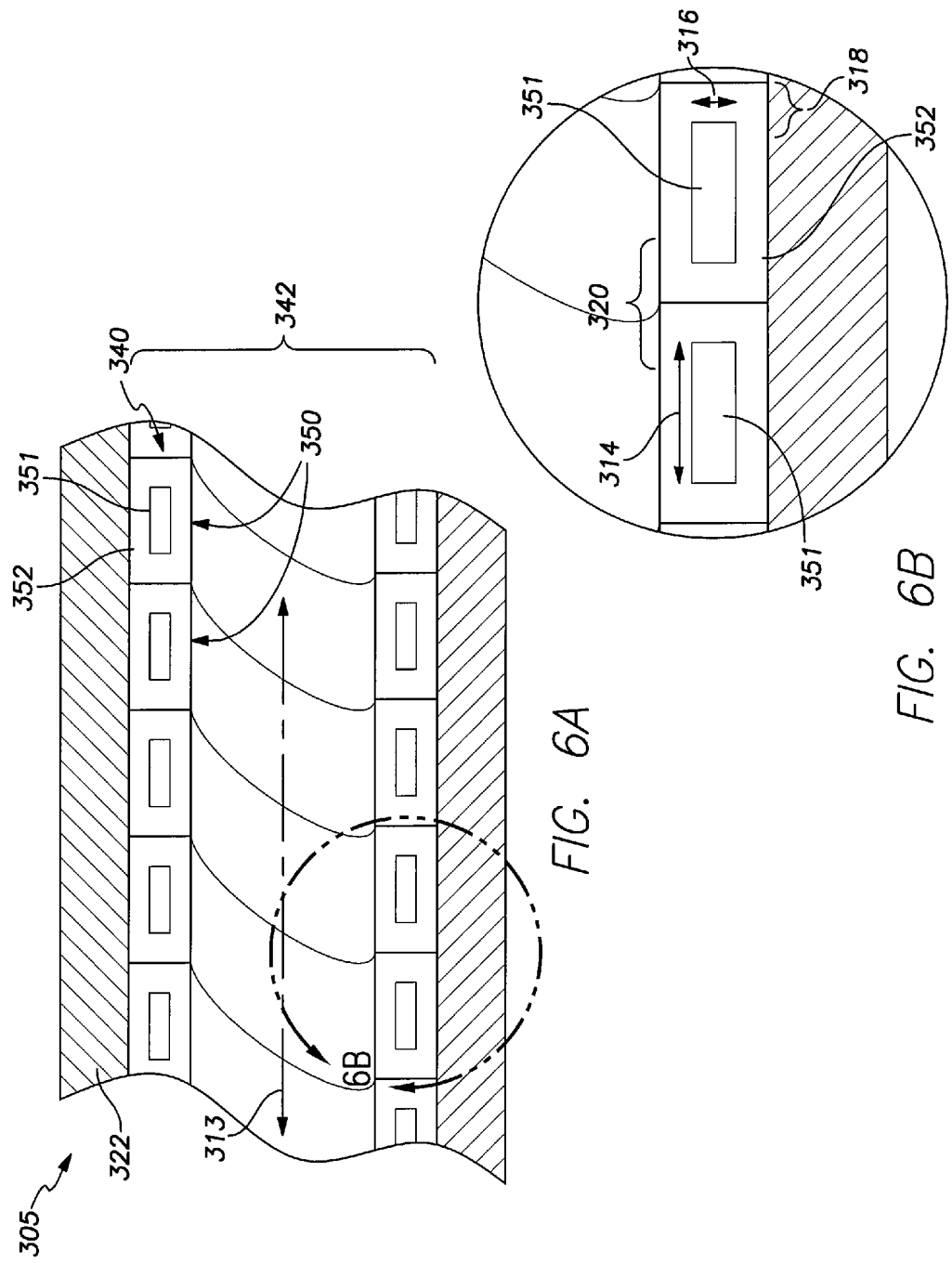

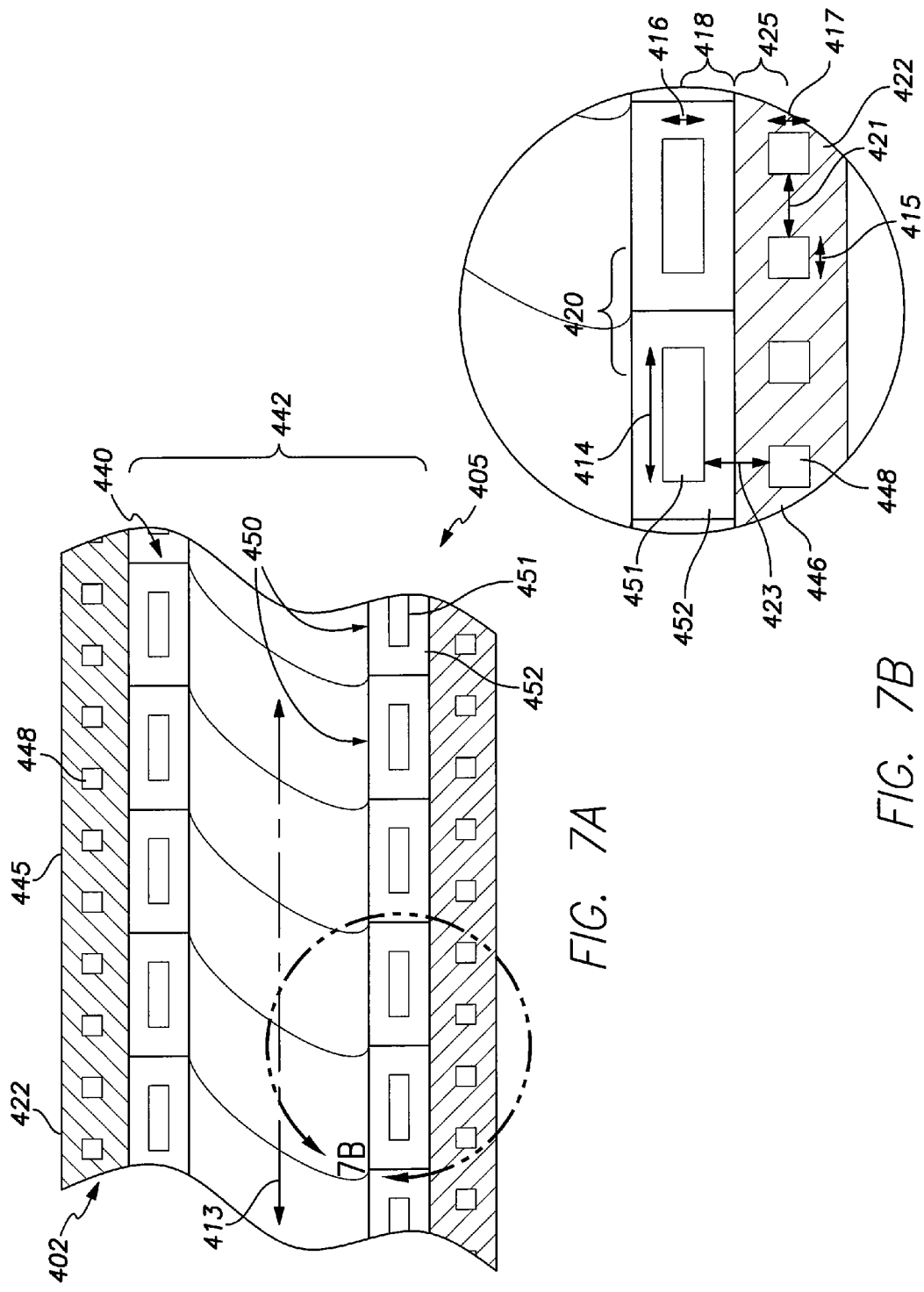

MRI COMPATIBLE IMPLANTABLE LEAD WITH A DISTRIBUTED BAND STOP FILTER

CROSS REFERENCE TO RELATED APPLICATIONS

This application claims the benefit of U.S. Provisional Application Ser. No. 61/187,154, filed Jun. 15, 2009.

FIELD OF THE INVENTION

Embodiments of the present invention generally relate to implantable leads, and more particularly to an implantable lead that is compatible with a magnetic resonance imaging (MRI) scanner.

BACKGROUND OF THE INVENTION

A body implantable lead forms an electrical connection between a patient's anatomy and a pulse generator such as a cardiac pacemaker, an implantable cardioverter defibrillator (ICD), an appetite or pain suppression device, and the like. The lead includes a lead body comprising a tubular, flexible biocompatible, biostable insulative sheath or housing, such as formed of silicone rubber, polyurethane or other suitable polymer. One example of a lead body is a bipolar lead having a tip electrode and a ring sensing electrode. Generally bipolar leads include two coaxial conductors with insulation therebetween that are carried within the insulative housing. Another example of a lead body is a cardioverter/defibrillator lead that includes a sensing ring, a shocking right ventricle (RV) electrode, a shocking superior vena cava (SVC) electrode and a tip sensing/pacing electrode. The lead includes a multi-lumen housing, each lumen of which carries a separate conductor through the lead housing to each of the sensing ring, RV electrode, SVC electrode and tip electrode.

Magnetic resonance imaging (MRI) is commonly used as an efficient technique in the diagnosis of many injuries and disorders. MRI scanners provide a non-invasive method for the examination of internal structure and function. The MRI scanner includes a static magnetic field, a gradient magnetic field and a radio frequency (RF) magnetic field. The static magnetic field aligns protons of hydrogen atoms in the body, while the RF magnetic fields expose the protons to varying RF fields which cause the protons to spin and thus produce a faint signal that is detected by a receiver portion of the MRI scanner. The static magnetic field may have a field strength of between 0.2 and 3.0 Tesla. A nominal value of 1.5 Tesla is approximately equal to 15,000 Gauss. The time varying or gradient magnetic field may have a maximum strength of approximately 40 milli-Tesla/meters at a frequency of 0 5 KHz. The RF magnetic field may have a frequency between 8 and 215 MHz. For example, up to 20,000 watts may be produced at 64 MHz in a static magnetic field of 1.5 Tesla.

A concern has arisen regarding the potential interaction between the MRI environment and implantable leads and devices. In particular, implantable leads may experience RF-induced current. The RF induced current has been found to raise the temperature in the leads by 25 degree Centigrade or higher.

Heretofore, leads have been proposed for use with MRI-safe implantable medical devices. These proposed leads are coupled to, or have housed therein, a discrete resonant tuning module. The resonant tuning module includes a control circuit for determining a resonance frequency of the implantable device and an adjustable impedance circuit to change the combined resonant frequency of the medical device and the lead. The resonant circuit includes an inductor (L) coupled in parallel with a capacitor (C) to form a discrete LC circuit. The inductance and capacitance values of the inductor and capacitor are tuned approximately to the frequency of an expected RF magnetic field in an MRI scanner.

However, it remains challenging to implement discrete LC and L circuits within leads while still meeting performance requirements. For example, circuit size is a challenge as there is a continued desire to provide circuits that are small enough to be packaged inside the distal portion of a lead. Also, it is difficult to locate a discrete LC or L circuit in the distal or proximal end of a lead without changing the internal design of existing leads. Further, to implement the LC or L circuits in pacemakers, the circuit should be able to withstand large surges of energy such as when a shock is delivered by an external defibrillation. Other challenges include sensitivity to design variables in leads (e.g., shielding effect; subtle changes around the component may alter heating significantly), cost, and biocompatibility (e.g., Hermetic seal; Mechanical requirements).

It would be desirable to provide an implantable medical lead that is safely operated in an MRI environment. It would be further desirable to provide an improved implantable medical lead that may be operated in an MRI environment without the generation of significant heat in the lead. Furthermore, other desirable features and characteristics will become apparent from the subsequent detailed description of the invention and the appended claims, taken in conjunction with the accompanying drawings and this background of the invention.

BRIEF DESCRIPTION OF THE INVENTION

In accordance with one embodiment, an implantable lead is provided that comprises a lead connector and an electrode configured to perform at least one of a sensing operation and delivery of electrical energy. The implantable lead includes a lead body having a proximal end portion and a distal end portion with the connector located at the proximal end and the electrode located at the distal end. The lead body has a length that includes a lumen that extends longitudinally between the distal and proximal end portions. The implantable lead further includes a coil conductor having spiral sections that are wound within the lumen and extend from the lead connector along the lumen. The coil conductor couples the lead connector to the electrode. The coil conductor has an insulation material provided on at least a segment of the coil conductor. The insulation material of the coil conductor has a dielectric constant set such that the coil conductor forms a distributed band stop filter when exposed to a known RF magnetic field. The dielectric constant may be at least 5 and up to 100.

In accordance with another embodiment, an implantable lead is provided that comprises a lead connector and an electrode configured to perform at least one of a sensing operation and delivery of electrical energy. The implantable lead includes a lead body having a proximal end portion and a distal end portion with the connector located at the proximal end and the electrode located at the distal end. The lead body of the implantable lead has a length that includes a lumen that extends longitudinally between the distal and proximal end portions. The implantable lead further includes a coil conductor having concentric inner and outer layers that are wound in and located within the lumen. The coil conductor couples the lead connector to the electrode. The coil conductor has an insulation material provided on at least a segment of the coil conductor with the inner and outer layers each comprising at least one filar that is coated with the insulation material to form a dielectric layer between adjacent spiral sections of the coil conductor.

In accordance with an alternative embodiment, a method is provided for manufacturing an implantable lead that has a proximal end portion and a distal end portion that has a length that extends therebetween. The lead body has a length that includes a lumen extending longitudinally between the distal and proximal end portions. The method includes providing a coil conductor having at least one filar that is wound into spiral sections with the filar having an insulation coating thereon and forming a dielectric layer between adjacent spiral sections of the coil conductor so that when exposed to a known RF magnetic field, the coil conductor operates as a distributed band stop filter. The coil conductor exhibits predetermined amounts of inductance and capacitance based on filter parameters. The method includes controlling the filter parameters such that the predetermined amount of capacitance and the predetermined amount of inductance, exhibited by the coil conductor, form a band stop filter. The method further includes locating the coil conductor with the lumen of the lead body.

In accordance with another alternative embodiment, a coil conductor is provided for an implantable lead that has distal and proximal end portions and a lumen that extends longitudinally therebetween. The coil conductor comprises a filar that is wound into spiral sections to fit within and extend along the lumen in the lead. The filar has an insulation coating provided thereon with the insulation coating forming a dielectric layer between adjacent spiral sections of the filar. The insulation coating of the filar comprises tantalum oxide having a dielectric constant of at least 10.

BRIEF DESCRIPTION OF THE DRAWINGS

FIG. 2 illustrates a side-sectional view of a portion of the lead assembly of FIG. 1.

FIG. 3 illustrates an end sectional view of the lead assembly of FIG. 1 taken long line 3-3 in FIG. 2.

FIG. 4A illustrates a side-sectional view of a portion of a distributed band stop filter formed in accordance with an alternative embodiment of the present invention and FIG. 4B illustrates an expanded side-sectional view of a portion of the distributed band stop filter illustrated in FIG. 4A.

FIG. 5 illustrates a side-sectional view of a portion of a distributed band stop filter formed in accordance with an embodiment of the present invention.

FIG. 6 illustrates a side-sectional view of a portion of a distributed band stop filter formed in accordance with an alternative embodiment.

FIG. 7A illustrates a side-sectional view of a portion of a distributed band stop filter as formed in accordance with an alternative embodiment and FIG. 7B illustrates an expanded side-sectional view of a portion of the distributed band stop filter illustrated in FIG. 7A.

DETAILED DESCRIPTION OF THE INVENTION

The following description presents embodiments of the present invention. This description is not to be taken in a limiting sense but is made merely for the purpose of describing the general principles of the invention whose scope is defined by the appended claims. Although the following embodiments are described principally in the context of cardioverting/defibrillating electrodes, the invention may be applied to other electrode structures, for example, sensing ring electrodes. As further examples, embodiments may be implemented in pacemaker applications in connection with sensing and/or pacing pulse delivery. For example, embodiments may be used with a pacemaker, cardioverter, defibrillator, and the like. As other examples, embodiments may be used with devices that suppress an individual's appetite, reduce or offset pain associated with chronic conditions and control motor skills for handicap individuals.

In-vitro tests and modeling have suggested that a high impedance band stop filter (at MRI RF frequencies) connected in series with the conductors of a lead will reduce RF heating. Heating reduction is independent of coiling effect, lead length, lead type and lead path etc. The implementation of a band stop filter at the RF frequency of an MRI scanner (e.g. 64 MHz in 1.5 T and/or 128 Mhz in 3 T) can be done through an LC resonant circuit network formed from self resonant inductors and parasitic capacitance and resistance.

Insulated wire technologies afford RF heating reduction with insulated co-axial or co-radial leads at non-clinical configurations in gel. The advantages of insulated wires are easy implementation in current leads structures, low cost, mechanical reliability and the like. To overcome certain shortcomings, it is desirable to achieve high impedance within a short coil length of a lead body (e.g., less than 25 cm for brady leads) in order to limit heating due to the coiling effect.

The distributed band stop filter is created by increasing parasitic capacitance of the insolated coil forming a LC resonant circuit with self resonant frequency near the MRI RF frequency and still utilize relatively short multi-filar coils. The distributed band stop filters discussed hereafter represent various embodiments to increase the parasitic capacitance of the insulated coil structure while reducing the length for multi-filar coated coils.

Figure 1:
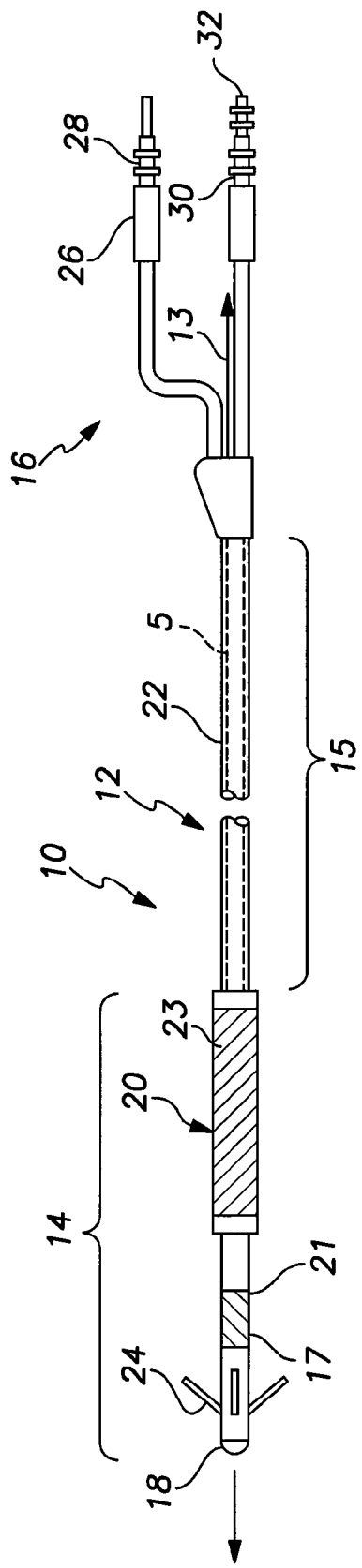
FIG. 1 illustrates a lead assembly formed in accordance with an embodiment of the present invention.

FIG. 1 illustrates a body implantable lead assembly 10 that includes a distributed band stop filter 5 formed in accordance with an embodiment of the present invention. The lead assembly 10 includes a lead body 12 having a distal end portion 14, an intermediate portion 15 and a proximal end portion 16. The lead body 12 has a length that extends along a longitudinal axis 13 between the distal and proximal end portions 14 and 16. The term longitudinal axis encompasses both linear and non-linear axes. The longitudinal axis 13 of the lead body 12 extends along a curved path that changes as the lead body is flexed, bent and otherwise manipulated. The lead assembly 10 includes a tip electrode 18, a coil electrode 20 and a sensing electrode 21 in the form of a ring positioned proximate to the tip electrode 18. The lead body 12 includes an insulating sheath or housing 22 of a suitable insulative, biocompatible, biostable material such as, for example, silicone rubber or polyurethane, extending substantially the entire length of the lead body.

The lead body 12 includes the distributed band stop filter 5 along the distal end portion 14 and the intermediate portion 15. Optionally, the distributed band stop filter 5 may be provided at only one of the distal end portion 14 and the intermediate portion 15. Various embodiments for distributed band stop filters 5 are illustrated and discussed hereafter. It should be recognized that FIG. 1 illustrates merely one example of the type of lead assembly that may incorporate a distributed band stop filter 5 in accordance with embodiments of the present invention. Optionally, the distributed band stop filter 5 may be implemented within pacemaker leads, defibrillation leads, cardioversion leads, neurostimulation leads, electrophysiology leads, hemodynamic leads, and the like. The distributed band stop filter 5 may also be used with subcutaneous patches, paddle shaped electrodes and the like.

Returning to FIG. 1, the electrode 20 is disposed along the distal end portion 14 of the lead body 12 at an electrode retention area. In the example of FIG. 1, the electrode 20 is shown to have a circumference or diameter that is greater than the circumference or diameter of the housing 22. Optionally, the electrode retention area may be formed as an offset notched into the housing 22 by an amount corresponding to the thickness of the electrode 20, such that an outer envelope of the electrode 20 substantially correspond to the outer envelope of the housing 22 (such as shown by the sensing electrode 21). The electrode 20 may be formed as a single continuous cylindrical band or have multiple spiral sections 23 wound continuously about the lead body 12 in a helical arrangement. The electrode 20 has an exposed outer electrode surface that is configured to perform at least one of a sensing operation and delivery of an electrical stimulus. Gaps between the spiral sections 23 may be filled with a conductive biocompatible material. The sensing electrode 21 may be formed as a single continuous cylindrical band or provided with multiple sections 17 that may also be wound about the lead body 12 in a helical arrangement. The sensing electrode 21 is configured to perform at least one of a sensing and pacing pulse delivery operation. The connector pin 32 and the inner coil conductor 40 are hollow. A stylet may be passed through the hollow connector pin 32 and an open core 45 of the inner coil conductor 40. The stylet enables the physician to orient the distal end portion 14 of the lead assembly 10 and to position the tip electrode 18, such as under fluoroscopy at a desired location in the heart. When both pacing and sensing functions are performed by the tip electrode 18, the inner coil conductor 40 provides a bidirectional electrical transmission link between a pacemaker/defibrillator and the tip electrode 18. Where a ring sensing electrode such as the electrode 21 is utilized, a separate coil conductor (not shown) is incorporated in the lead assembly 10 for connecting a terminal on the connector 30 with the sensing electrode.

Optionally, the housing 22 may include, along the distal end portion 14, a plurality of projecting tines 24 that function to interlock the lead assembly 10 within the tissue and thereby prevent inadvertent displacement of the distal end portion 14 once the lead assembly 10 is implanted. While the tines 24 represent one anchoring means, optionally other anchoring means may be utilized. For example, the anchoring means may constitute fins, a screw-in helix, or some other suitable anchoring means may be used instead, including one or more S-shaped bends along the distal end portion, without tines, for anchoring. Alternatively, the tines 24 and all other anchor means may be removed entirely.

The proximal end portion 16 includes a lead connector 26 for coupling the lead assembly 10 to a device. The lead connector 26 comprises a first connector 28, which may conform to the DF-1 standard when used for supplying electrical impulses for defibrillation, and a second connector 30, which may conform to the IS-1 standard when connecting a pacemaker/defibrillator to the tip electrode 18 and sensing electrode 21. The second connector 30 includes a connector pin 32. The lead connector 26 may vary in structure based upon the type of device connected thereto.

FIG. 2 illustrates a side-sectional view of a portion of the distributed band stop filter 5 formed in accordance with an embodiment of the present invention. The filter 5 may be formed along the entire lead assembly 10, the electrodes 18, 21 and 20 or in an area proximate to, or in one or more of the distal, intermediate and proximal portions 14-16. A single filter 5 may be included in the lead assembly 10, or multiple separate filters 5 may be separately distributed along the lead assembly 10. FIG. 3 illustrates an end sectional view along line 3-3 in FIG. 2. The lead body 12 is formed with a central lumen 42 and an outer lumen 43, that both extend between the distal and proximal end portions 14 and 16. The central and outer lumens 42 and 43 are separated by an insulated sleeve 44. The central lumen 42 receives an inner coil conductor 40, while the outer lumen 43 receives an outer coil conductor 46. The outer coil conductor 46 has a proximal end that is connected to the first connector 28 for delivering an electrical charge generated by the electrode 20. The inner coil conductor 40 is coupled to the connector pin 32 and the tip electrode 18.

As shown in FIG. 2, the inner and outer coil conductors 40 and 46 are each helical in shape with a series of spiral sections 50 and 56 that are wound within the central and outer lumens 42 and 43, respectively. The spiral sections 50 of the inner coil conductor 40 have an insulation material 52 provided over one or more conductive filars 51. The spiral sections 56 of the outer coil conductors 46 have an insulation material 53 provided over one or more conductive filars 54. Optionally, the insulation material 52 and 53 may be provided only over separate discrete segments of the coil conductors 40 and 46, such as in a zebra coil configuration. The insulation material 52 forms a dielectric layer between adjacent spiral sections 50 of the coiled conductor 40. The insulation material 53 forms a dielectric layer between adjacent spiral sections 56 of the coil conductor 46. The insulation material 52 and 53 may be provided about individual filar 51 and 54 through a coating process, extrusion, and the like. The individual filars of the coil conductors 40 and 46 may have circular, rectangular, square or oval cross-section and may be formed from MP35N, tantalum or another biocompatible conductive material that facilitates the coating process for the insulation materials 52 and 53.

The insulation materials 52 and 53 are formed from materials that have relatively high dielectric constants, such as between 5 and 100. Optionally, the insulation material 52 and 53 may be formed of a material that preferably has a dielectric constant between 20 and 60. For example, the insulation material 52 and 53 may be formed from polyimide, tantalum oxide or another biocompatible insulation material that has a dielectric constant of at least 5.

In accordance with the embodiments described herein, a distributed band stop filter is provided along an entire length of the lead body 12 or along a segment of the lead body 12, and is tuned to predetermine with RF frequencies, such as to 64 MHz when indicated for use in an MRI scanner having a 1.5 Tesla strength magnet or to 128 MHz when indicated for use in an MRI scanner having a magnet strength of 3 Tesla.

The distributed band stop filter forms distributed self resonant inductors along the entire length of the lead body by coating the filars of the coil conductors with insulation material. The distributed band stop filter is tuned by controlling the amount of parasitic capacitance to achieve a predetermined level thereof between the various components within the lead. Parasitic capacitance may arise through interaction of various elements. For example, parasitic capacitance may exist between adjacent spiral sections of a coil conductor. As a further example, parasitic capacitance may exist between the spiral sections of an inner coil and the spiral sections of an outer coil. Parasitic capacitance may also exist between the coil conductor and other conductive layers and components within the lead. The parasitic capacitance may be increased to a level sufficient to permit the resonant inductance to be decreased while still achieving a desired tuned LC network at a desired RF frequency (e.g., 64 MHz or 128 MHz).

As the parasitic capacitance is increased, the resonance inductance may be decreased. By reducing the resonant inductance, the dimensions of the overall lead may be maintained relatively small. The parasitic capacitance may be increased by changing various filter parameters. For example, the following filter parameter changes may be implemented to increase the parasitic capacitance, namely increasing the dielectric constant of the insulation materials surrounding the filars of the core conductors, increasing the effective capacitance surface area of the filars that contributes to capacitance, reducing the distance between surfaces that interact as capacitance plates (e.g., between adjacent filars, between a filar and a fiber in the outer layer, between adjacent coils and the like) by reducing the thickness of the dielectric coating, and by using conductive materials that have higher resistivity. As one example, by using tantalum oxide as the insulation coating about the filars, a coating is provided with a high dielectric constant which allows the thickness of the insulation coating to be reduced thereby reducing the distance between adjacent filars and adjacent spiral sections of the coil conductor. As another option, the filars of the inter-coil may be made of tantalum to facilitate the tantalum oxide coating.

FIG. 4 illustrates a side-sectional view of a portion of a distributed band stop filter 105 formed in accordance with an alternative embodiment of the present invention. The band stop filter 105 is formed within an alternative lead structure in which a single coil conductor 140 is inserted into a central lumen 142 within the housing 122 of the lead 112. The coil conductor 140 has a helical shape with a series of spiral sections 150 that are wound within the central lumen 142. Each of the spiral sections includes one or more conductive filars 151 that are individually coated with an insulation coating 152. In the example of FIG. 4, a single filar 151 with insulation coating 152 is illustrated.

A portion (denoted at Detail A) is expanded within FIG. 4 to better illustrate the construction and spacing of the filars 151 and insulation coating 152 that facilitate the construction of the distributed band stop filter 105. Each filar 152 has a width 114 and a height 116. In the example of FIG. 4, the width 114 is measured in a direction substantially parallel to the longitudinal axis 113 of the lead 112, while the height 116 is measured in a transverse or radial direction relative to the longitudinal axis 113. Each filar 151 is surrounded by the insulation coating 152 which has a thickness 118 that is substantially uniform about the corresponding filar. The thickness 118 of the insulation coating 152 also substantially conforms to the cross-sectional shape of the filar 151. For example, as shown in FIG. 4, the filar 151 has a rectangular shape and thus the insulation coating 152 similarly has a substantially rectangular shape. It should be recognized that the insulation coating 152 may not have a cross-sectional shape that is identical to the cross-sectional shape of the filar 151, but instead may generally conform to the cross-sectional shape of the filar 151.

As illustrated in FIG. 4, the filars 151 that are adjacent to one another are separated by an inter-coil spacing 120 which corresponds to the distance between the adjacent filars 151 as measured along the longitudinal axis 113. The inter-coil spacing 120 is substantially filled with and determined by the thickness of the insulation coating 152. The spiral sections 150 experience parasitic capacitance between adjacent filars 151. The amount of parasitic capacitance exhibited by adjacent filars 151 is produced at least in part as a function of the height 116 of each filar 151, the inter-coil spacing 120 between adjacent filars 151, the dielectric constant of the material forming the insulation coating 152 and the resistivity of the material used to form the filars 151.

FIG. 5 illustrates a side-sectional view of a portion of a distributed band stop filter 205 formed in accordance with an embodiment of the present invention. The filter 205 may be formed anywhere along the lead assembly, in the area proximate to, or remote from the electrodes. The distributed band stop filter 205 of FIG. 5 is provided within a lead of the type having an outer housing 222 with a single central lumen 242 formed therein. The central lumen 242 receives a coil conductor 240 that is formed with a two layered construction, namely with concentric inner and outer layers 230 and 232. The outer layer 232 comprises one or more filars 251, while the inner layer 230 comprises one or more filars 254. Each filar 251 and 254 is surrounded by a corresponding insulation coating 252 and 253, respectively. An expanded portion (denoted Detail B) is illustrated to better discuss the relation and structure of the inner and outer layers 230 and 232. As shown in expanded Detail B, the filars 251 have a width 214 and a height 216, while the filars 254 have a width 234 and a height 236. The widths 214 and 234 are measured in a direction parallel to the longitudinal axis 213, while the heights 216 and 236 are measured in a direction transverse or extending radially with respect to the longitudinal axis 213 of the housing 222. In the present example, the widths 214 and 234 of the filars 251 and 254 in the outer and inner layers 232 and 230 are identical and common to one another. Optionally, the widths 214 and 234 may differ from one another and/or, the heights 216 and 236 may differ from one another.

The filars 251 with the outer layer 232 are separated by an inter-coil spacing 220 which is determined in part by the thickness 218 of the insulation coating 252. The filars 254 within the inner layer 232 have an inter-coil spacing 238 that is determined by and based upon the thickness of the insulation coating 253. The inter-coil spacing 230 and 238 are substantially double the thickness 218. The filars 251 and 254 are separated by an inter-layer spacing 244 that is dependent upon and determined by the thickness of the coating 252 and the thickness of the coating 253.

The inner and outer layers 230 and 232 of the coil conductor 240 exhibit an amount of parasitic capacitance that is in part dependent upon the interrelation and interaction of the components illustrated within expanded Detail B. The parasitic capacitance is controlled in part by the dielectric constants of the insulation coatings 252 and 253, by the inter-coil spacings 220 and 238, by the interlayer spacings 244, by the widths 214 and 234 of the filars 251 and 254, as well as by the heights 216 and 236 of the filars 251 and 254.

In the embodiment of FIG. 5, the coil conductor 240 utilizes two layers 230 and 232 of flat wire that are surrounded with insulated material to increase the surface area within the coil conductor 240 that contributes to parasitic capacitance.

FIG. 6 illustrates a side-sectional view of a portion of a distributed band stop filter 305 formed in accordance with an alternative embodiment. The filter 305 is formed within a lead housing 322 that has a single central lumen 342. The central lumen 342 receives a single coil conductor 340 that is formed in a helical shape with a series of spiral sections 350. The lead housing 322 extends along a longitudinal axis 313. The coil conductor 340 is formed with one or more filars 351 that are surrounded by an insulation coating 352. In the embodiment of FIG. 6, as shown in Detail C, the filars 351 are formed with a rectangular shape having a width 314 and a height 316. The width 314 is measured in a direction parallel to the longitudinal axis 313, while the height 316 is measured in the transverse or radial direction relative to the longitudinal axis 313. Adjacent filars 351 are separated by an inter-coil spacing 320 that is determined by the thickness 318 of the insulation coating 352.

The coil conductor 340 exhibits parasitic capacitance that is based in part upon the structure and interaction between adjacent spiral sections 350. By way of example, the parasitic capacitance between adjacent filars 351 is tuned by controlling the height 316, inter-coil spacing 320, dielectric constant of the insulation coating 352 and resistivity of the filars 351. For example, as the inter-coil spacing 320 is increased, the parasitic capacitance decreases. As the dielectric constant of the insulation coating 352 is increased, the parasitic capacitance increases. As the height 316 of the filars 351 is increased, the effective capacitance surface areas of adjacent filars 351 similarly is increased, thereby increasing the parasitic capacitance.

FIG. 7 illustrates a side-sectional view of a portion of a distributed band stop filter 405 as formed in accordance with an alternative embodiment. The band stop filter 405 is provided within a lead assembly having a housing 422 that includes a central lumen 442 which receives a coil conductor 440. The coil conductor 440 has multiple spiral sections 450 formed in a helical shape. The spiral sections 450 of the coil conductor 440 have one or more conductive filars 451 that are surrounded by insulation coating 452. The housing 422 extends along a longitudinal axis 413.

The housing 422 also includes a conductive liner 402 arranged concentrically about the coil conductor 440. The conductive liner 402 is formed from an insulation material 446 that surrounds one or more conductive fibers 448. The conductive fibers 448 may represent conductive tubing or a conductive braid with the fibers 448 being arranged in a mesh configuration and then embedded within the insulation material 446. A portion (denoted Detail D) is expanded to better illustrate the interrelation and structure of the coil conductor 440 and housing 422. The filars 451 have widths 414 and heights 416, as measured along and transverse to the longitudinal axis 413, respectively. The filars 451 within adjacent spiral sections 450 are separated by an inter-coil spacing 420. The fibers 448 in the conductive liner 402 have widths 415 and heights 417. The fibers 448 may have a circular, rectangular, square or oval cross-section. In the example of FIG. 7, the fibers 448 have a square cross-section and thus the widths 415 and heights 417 equal one another. Alternatively, the heights 417 may be greater than the widths 415 or alternatively, the widths 415 may be greater than the heights 417. Optionally, the widths 415 of the fibers 448 may be equal to or greater than the widths 414 of the filars 451.

The fibers 448 are separated by an inter-fiber spacing 421. The filars 451 are separated from the nearest fiber 448 by a filar-to-fiber spacing 423. The filar-to-fiber spacing 423 is dependent in part the thickness 418 of the insulation coating 452 and in part on the thickness 425 of the insulation material 446 surrounding the fibers 448. The insulation material 446 and insulation coating 452 may be formed of the same or different materials. In one embodiment, the insulation coating 452 and insulation material 446 are formed of material with the same high dielectric constant, such as tantalum oxide.

The filars 451 and fibers 448 interact with one another to exhibit a predetermined amount of parasitic capacitance. The parasitic capacitance exhibited by the configuration of FIG. 7 includes a component of parasitic capacitance associated with the interaction between adjacent filars 451 and a component of parasitic capacitance associated with the interaction between the filars 451 and the fibers 448. For example, inter-coil parasitic capacitance is based upon the height 416 of adjacent filars 451, the inter-coil spacing 420, the dielectric constant of the insulation coating 452 and the resistivity of the filars 451. A filar-to-fiber parasitic capacitance is based on the widths 414 of the filars 451, the widths 415 of the fibers 448, the filar-to-fiber spacing 423, the resistivities of the filar 451 and fiber 448, and the dielectric constants of the insulation coating 452 and insulation material 446.

In the embodiment of FIG. 7, the fibers 448 may be braided or metalized PTFE/ETFE tubing. The fibers 448 are arranged concentrically about the coil conductor 440 to increase the surface area of the capacitive electrodes and thus increase the parasitic capacitance.

Figure 8:
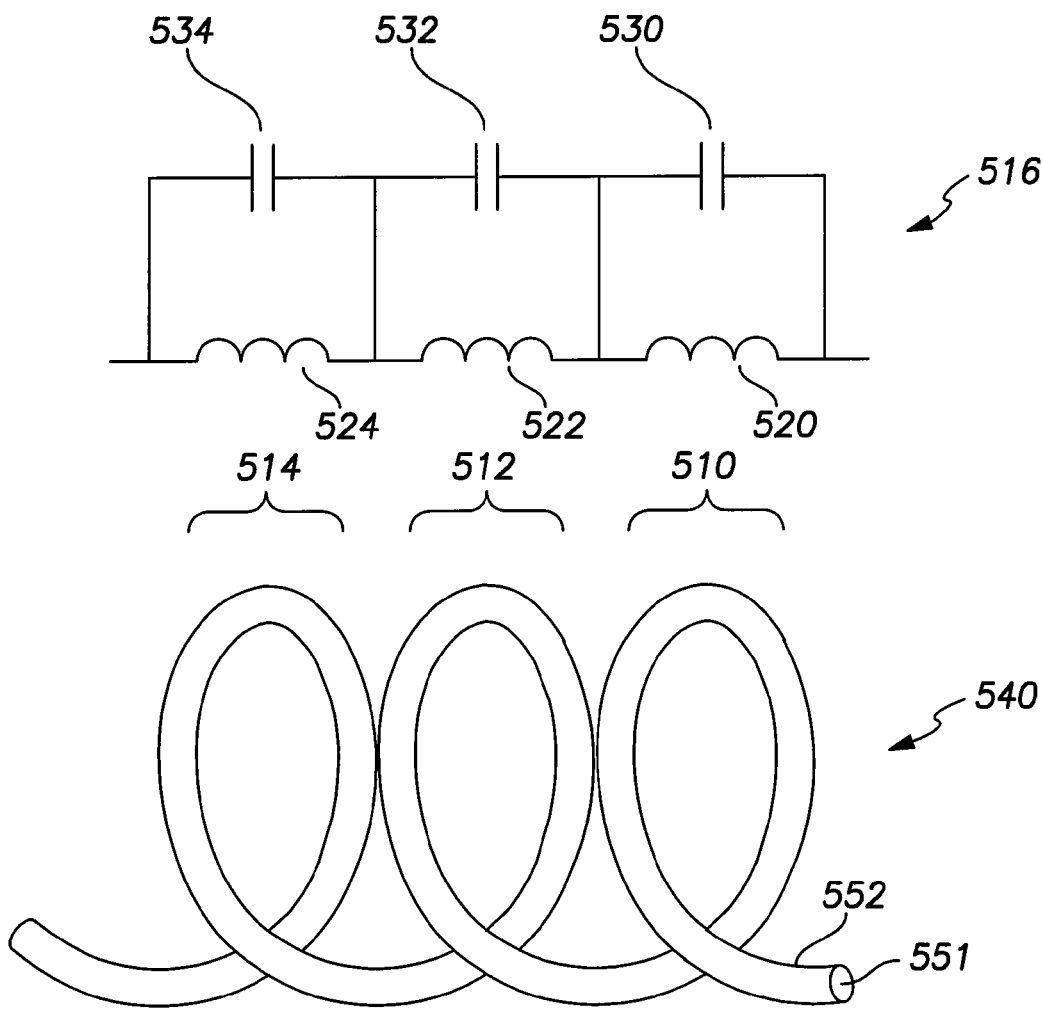
FIG. 8 illustrates a representation of a portion of a coil conductor having a single filar that is coated with an insulation coating.

FIG. 8 illustrates a representation of a portion of a coil conductor 540 having a single filar 551 that is coated with an insulation coating 552. The coil conductor 540 is wound into spiral sections 510, 512 and 514. FIG. 8 also illustrates an LC network 516 that is representative of the electrical behavior exhibited by the coil conductor 540 when exposed to an RF magnetic field, such as the 64 MHz RF magnetic field of a 1.5 Tesla MRI scanner. When exposed to an RF magnetic field, the spiral sections 510, 512 and 514 exhibit induction properties and capacitive properties. In the LC network 516, a series of inductors 520, 522 and 524 are joined with a series of capacitors 530, 532 and 534. The inductor 520 and capacitor 530 model the electrical performance of the spiral section 510. The inductor 522 and capacitor 532 model the electrical performance of the spiral section 512, while the inductor 524 and capacitor 534 model the electrical performance of the spiral section 514. By way of example, the capacitors 530, 532 and 534 represent the parasitic capacitance experienced by the corresponding spiral sections 510, 512 and 514 due 1) to interaction with one another, 2) with other coil conductors, 3) with other components with the lead and the like. The inductors 520, 522 and 524 represent the resonant inductance experienced by the corresponding spiral sections 510, 512 and 514 when exposed to an RF magnetic field.

The filter parameters of the LC network 516 are set to operate as an LC resonant circuit tuned to a frequency of a known RF magnetic field, such as 64 MHz or 128 MHz. By tuning the LC network 516 to function as an LC resonant circuit, the entire coil conductor 540 or the tuned segment(s) of the coil conductor 540 operates as a distributed band stop filter (in accordance with one of the embodiments discussed above). As a distributed band stop filter, the coil conductor 540 limits heating of the lead that might otherwise occur. The inductance and capacitance of the effective inductors and capacitors in the LC network 516 is adjusted by adjusting various filter parameters. For example, the filar 551 may be modeled as a plate of a capacitor, while the insulation coating 552 represents a dielectric layer of a capacitor that is created between adjacent spiral sections (e.g., 512 and 514) of the coil conductor 540. The filter parameters may be controlled such that a predetermined amount of capacitance that is exhibited by the coil conductor 540 and a predetermined amount of inductance that is exhibited by the coil conductor 540 form a band stop filter. The control operation may include adjusting at least one parameter as follows: 1) increasing a dielectric constant of the insulation material; 2) increasing a surface area the filar that contributes to the amount of parasitic capacitance; 3) reducing an inter-coil spacing between adjacent spiral sections; and 4) increasing a resistivity of the filar. As one example, the filter parameters may be set such that the parasitic capacitance exhibited by the distributed band stop filter is at least 10 pF.

Figure 9A:
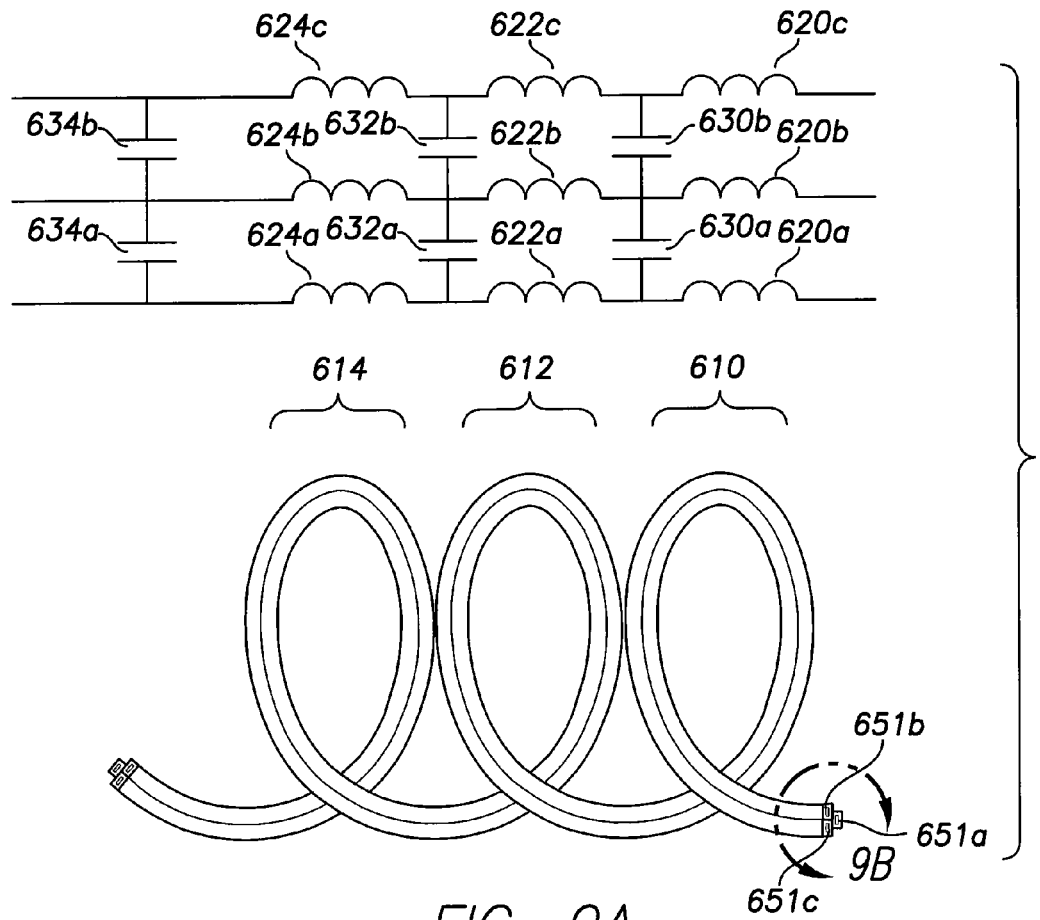
FIG. 9A illustrates a representation of a portion of a multi-filar coil conductor having multiple filars (e.g., three) that are each individually coated with an insulation coating
Figure 9B:
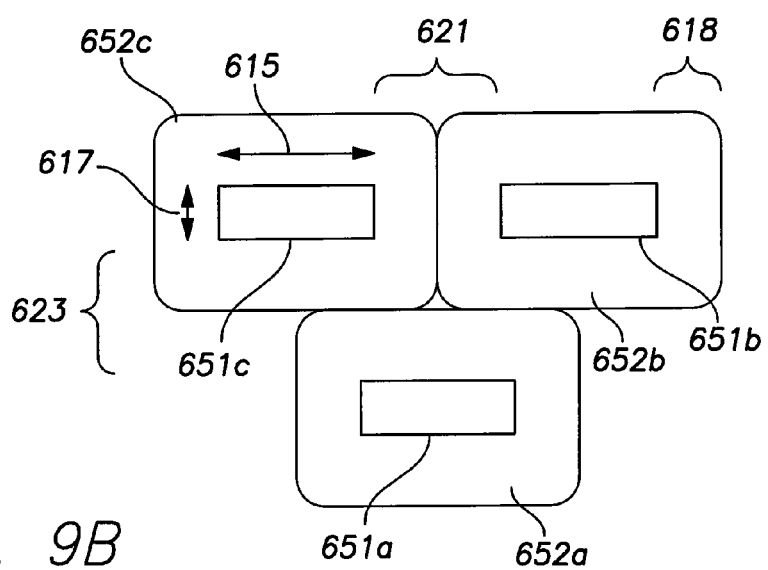
FIG. 9B illustrates an expanded view of a portion of an equivalent circuit model of the multi-filar coil conductor illustrated in FIG. 9A.

FIG. 9 illustrates a representation of a portion of a multi-filar coil conductor 640 having multiple filars 651*a*-651*c* (e.g., three) that are each individually coated with an insulation coating 652. The coil conductor 640 is wound into spiral sections 610, 612 and 614. Each spiral section 610, 612 and 614 includes all three coated filars 651*a*-651*c*. Detail E illustrates the construction of the filars 651*a*-651*c* and the corresponding insulation coatings 652*a*-652*c*. Each filar 651*a*-651*c* has a flat or rectangular shape with a width 615 and height 617, and inter-filar spacings 621 and 623 as measured between adjacent filars. The insulation coatings 652*a*-652*c* have a thickness 618.

FIG. 9 also illustrates an LC network 616 that is representative of the electrical behavior exhibited by the multi-filar coil conductor 640 when exposed to an RF magnetic field, such as the 64 MHz RF magnetic field of a 1.5 Tesla MRI scanner. When exposed to an RF magnetic field, each of the filars 651*a*-651*c* within the spiral sections 610, 612 and 614 exhibit induction properties and capacitive properties. In the LC network 616, a series of inductors 620*a*-620*c*, 622*a*-622*c* and 624*a*-624*c* are joined with a series of capacitors 630*a*-630*b*, 632*a*-632*b* and 634*a*-634*b*. The inductors 620*a*-620*c* and capacitors 630*a*-630*b* model the electrical performance of the spiral section 610. The inductors 622*a*-622*c* and capacitors 632*a*-632*b* model the electrical performance of the spiral section 612, while the inductors 624*a*-624*c* and capacitors 634*a*-634*b* model the electrical performance of the spiral section 614. By way of example, the capacitors 630*a*-630*b*, 632*a*-632*b* and 634*a*-634*b* represent the parasitic capacitance experienced by the corresponding spiral sections 610, 612 and 614 due to interaction with one another, with other coil conductors, with other components with the lead and the like, when exposed to a known RF magnetic field. The inductors 620*a*-620*c*, 622 and 624 represent the resonant inductance experienced by the corresponding spiral sections 610, 612 and 614 when exposed to a known RF magnetic field.

The LC network 616 is tuned to operate as an LC resonant circuit tuned to a frequency of a known RF magnetic field, such as 64 MHz or 128 MHz. By tuning the LC network 616 to function as an LC resonant circuit, the entire coil conductor 640 or the tuned segment of the coil conductor 640 operates as a distributed band stop filter. As a distributed band stop filter, the coil conductor 640 limits heating of the lead that might otherwise occur. The inductance and capacitance of the inductors and capacitors in the LC network 616 is adjusted by adjusting various filter parameters of the distributed band stop filter. For example, each of the filars 651*a*-651*c* may be considered a plate of a capacitor, while the insulation coatings 652*a*-652*c* form a dielectric layer of a capacitor that is created between adjacent spiral sections (e.g., 612 and 614) of the coil conductor 640.

The filter parameters may be controlled such that a predetermined amount of capacitance that is exhibited by the coil conductor 640 and a predetermined amount of inductance exhibited by the coil conductor 640 forms a band stop filter. The control operation may include adjusting at least one parameter as follows: 1) increasing a dielectric constant of the insulation material; 2) increasing a surface area the filar that contributes to the amount of parasitic capacitance; 3) reducing an inter-coil spacing between adjacent spiral sections; 4) increasing a resistivity of the filar and; 5) reducing an inter-filar spacing between adjacent filars within a coil conductor.

Figure 10:
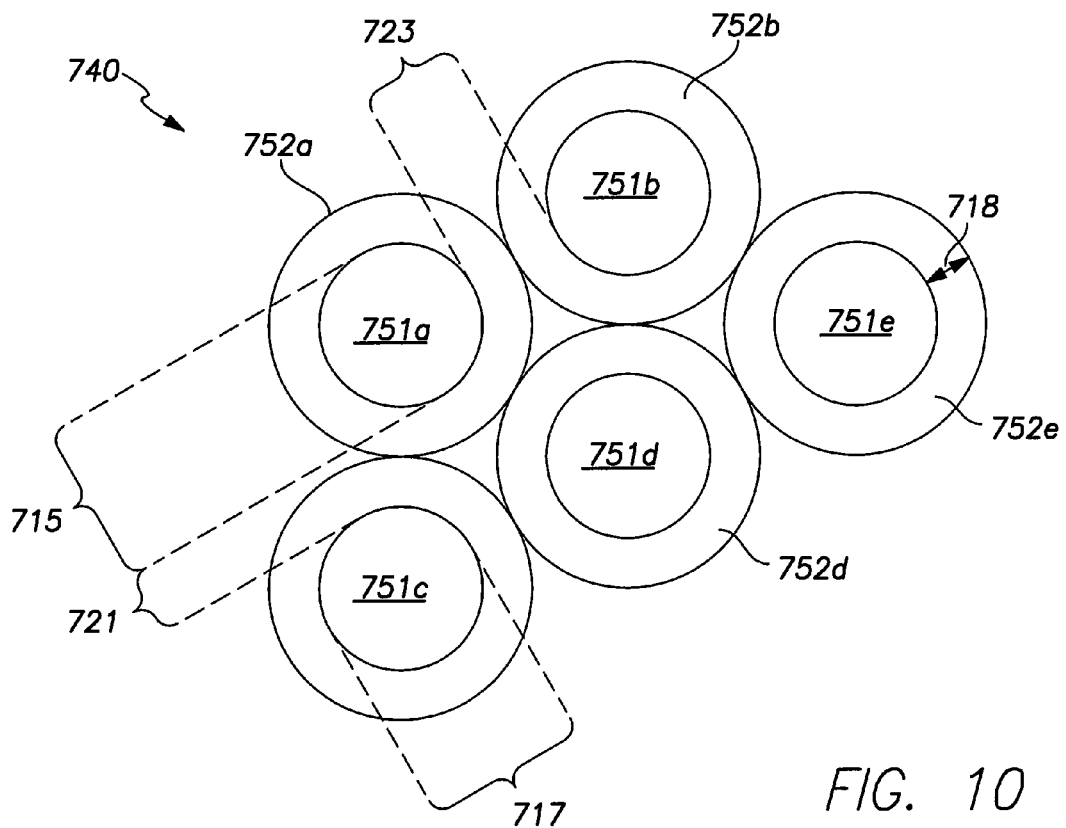
FIG. 10 illustrates a cross-sectional view of a multi-filar coil conductor formed in accordance with an alternative embodiment.

FIG. 10 illustrates a cross-sectional view of a multi-filar coil conductor 740 formed in accordance with an alternatively embodiment. The coil conductor 740 has multiple filars 751*a*-751*e* (e.g., five) that are each individually coated with an insulation coating 752*a*-752*e*. Each filar 751*a*-751*e* has a circular cross-sectional shape with an effective capacitance width 715 and an effective capacitance height 717, and inter-filar spacings 721 and 723 as measured between adjacent filars. The insulation coatings 752*a*-752*e* has a thickness 718. Optionally, one or more of the coatings 752*a*-752*e* may have a different thickness 718 than a thickness of the other coatings 752*a*-752*e*. Each of the filars 751*a*-751*e* may be still considered a plate of a capacitor where the effective capacitance surface area corresponds to the width 715 or height 717 depending upon the location of the adjacent component that is interacting with the filars 751*a*-751*e* to create the parasitic capacitance effect.

Each of the filars 751*a*-751 exhibit induction properties and capacitive properties as discussed above. The inductance and capacitance is adjusted by adjusting various filter parameters. The filter parameters may be controlled such that a predetermined amount of capacitance that is exhibited by the coil conductor 740 substantially offsets a predetermined amount of inductance that is exhibited by the coil conductor 740. The control operation may include adjusting at least one parameter as follows: 1) increasing a dielectric constant of the insulation material; 2) increasing a surface area the filar that contributes to the amount of parasitic capacitance; 3) reducing an inter-coil spacing between adjacent spiral sections; 4) increasing a resistivity of the filar and; 5) reducing an inter-filar spacing between adjacent filars within a coil conductor.

Figure 11:
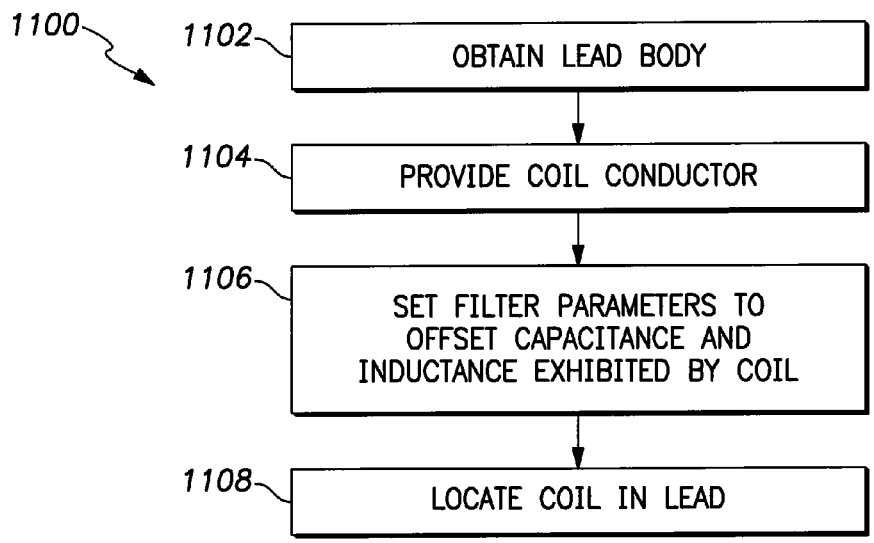
FIG. 11 illustrates a flow chart for a method of manufacturing an implantable lead.

FIG. 11 illustrates a flow chart for a method 1100 of manufacturing an implantable lead. The method 1100 comprises obtaining at 1102 a lead body having a proximal end portion and a distal end portion, and having a length extending therebetween. The lead body has a length that includes a lumen extending longitudinally between the distal and proximal end portions. At 1104 the method provides a coil conductor having at least one filar wound into spiral sections. The filar is coated with an insulation coating over at least a segment of the coil conductor. The insulation coating forms a dielectric layer between adjacent spiral sections of the coil conductor such that, when exposed to a known RF magnetic field, the coil conductor operates as a distributed band stop filter that exhibits predetermined amounts of inductance and capacitance based on filter parameters.

At 1106 the method includes controlling the filter parameters by setting the filter parameters such that the predetermined amount of capacitance that is exhibited by the coil conductor substantially offsets the predetermined amount of inductance that is exhibited by the coil conductor.

At 1108 the method includes locating the coil conductor within the lumen of the lead body. For example, the controlling operation includes adjusting at least one parameter as follows, namely 1) increasing a dielectric constant of the insulation material; 2) increasing a surface area the filar that contributes to the amount of parasitic capacitance; 3) reducing an inter-coil spacing between adjacent spiral sections; and 4) increasing a resistivity of the filar. As a further example, the controlling operation includes controlling the filter parameters that effect capacitance exhibited by the distributed band stop filter to increase the parasitic capacitance to at least 10 pF.

By increasing the parasitic capacitance, embodiments of the present invention enable a self resonating inductor to be designed with relatively small inductance. Inductance of the coil conductor is a function of the length of the segment of the filar(s) that is coated with insulation. As the length of the coated filar decreases, the inductance decreases. Thus, by reducing the inductance of the filter, shorter lengths of coated filars may be implemented, which allows shorter coils to be used. Short coil lengths are desirable in certain lead implementations, such as in a multi-filar inner coil of various tachycardia and brady leads.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. An implantable lead, comprising:
a lead connector;
an electrode configured to perform at least one of a sensing operation and delivery of electrical energy;
a lead body having a proximal end portion and a distal end portion, the connector located at the proximal end, the electrode located at the distal end, the lead body having a length that includes a lumen that extends longitudinally between the distal and proximal end portions;
a coil conductor having spiral sections that are wound within the lumen and extending from the lead connector along the lumen, the coil conductor coupling the lead connector to the electrode, the coil conductor having an insulation material provided on at least a segment of the coil conductor, the insulation material having a dielectric constant set to at least 5 and up to 100 such that the coil conductor forms a distributed band stop filter when exposed to a known RF magnetic field.

2. The lead of claim 1, wherein the lead body includes a conductive liner arranged concentric about the coil conductor, the conductive liner comprising an insulation material that surrounds conductive fibers, the conductive liner interacting with the coil conductor to collectively form the distributed band stop filter.

3. The lead of claim 2, wherein the conductive fibers are arranged in a mesh pattern.

4. The lead of claim 1, wherein the coil conductor comprises tantalum.

5. The lead of claim 1, wherein the insulation material is formed at least partially from at least one of polyimide and tantalum oxide coated on at least one filar in the coil conductor.

6. The lead of claim 1, wherein the coil conductor includes inner and outer layers that are arranged concentric with one another and are wound in the spiral sections, the inner and outer layers each comprising at least one filar that is coated with the insulation material forming the dielectric layer.

7. The lead, of claim 1, wherein the coil conductor forms the distributed band stop filter by exhibiting predetermined amounts of parasitic capacitance and inductance when exposed to a known RF magnetic field, the dielectric constant of the insulation material being set to tune the predetermined amount of parasitic capacitance to substantially offsets the predetermined amount of inductance when the lead is exposed to the known RF magnetic field.

8. The lead of claim 1, wherein the coil conductor operates as a distributed band stop filter is tuned to exhibit predetermined amounts of inductance and capacitance when exposed to the known RF magnetic field by setting values for filter parameters that include the dielectric constant of the insulation material, and at least one of an effective capacitance surface area of a filar in the coil conductor, an inter-coil spacing between adjacent spiral sections and a resistivity of the filar.

9. An implantable lead, comprising:
a lead connector;
an electrode configured to perform at least one of a sensing operation and delivery of electrical energy;
a lead body having a proximal end portion and a distal end portion, the connector located at the proximal end, the electrode located at the distal end, the lead body having a length that includes a lumen that extends longitudinally between the distal and proximal end portions;
a coil conductor having inner and outer layers that are wound in spiral sections and located within the lumen, the coil conductor coupling the lead connector to the electrode, the coil conductor having an insulation material provided on at least a segment of the coil conductor, the inner and outer layers each comprising at least one filar that is coated with the insulation material to form a dielectric layer between adjacent spiral sections of the coil conductor, the insulation material having a dielectric constant set to at least 5 and up to 100 such that the coil conductor forms a distributed band stop filter when exposed to a known RF magnetic field.

10. The lead of claim 9, wherein the filar has a non-circular cross-section having a width and height, the filar being oriented within the spiral sections such that the width extends substantially parallel to the length of the lead body and the height extends substantially transverse to the length of the lead body.

* * * * *